US008992890B2

(12) United States Patent
Pastorello et al.

(10) Patent No.: US 8,992,890 B2
(45) Date of Patent: Mar. 31, 2015

(54) ABSORBENT DRESSINGS WITH PAINKILLING ACTIVITY

(75) Inventors: Andrea Pastorello, Abano Terme (IT); Devis Galesso, Abano Terme (IT); Fabio Bettella, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 13/985,219

(22) PCT Filed: Feb. 13, 2012

(86) PCT No.: PCT/EP2012/052412
§ 371 (c)(1),
(2), (4) Date: Aug. 13, 2013

(87) PCT Pub. No.: WO2012/110456
PCT Pub. Date: Aug. 23, 2012

(65) Prior Publication Data
US 2013/0323183 A1    Dec. 5, 2013

(30) Foreign Application Priority Data

Feb. 15, 2011  (IT) .............................. PD2011A0043

(51) Int. Cl.
| | | |
|---|---|---|
| A61K 31/738 | (2006.01) | |
| A61K 31/192 | (2006.01) | |
| A61K 31/196 | (2006.01) | |
| A61K 31/717 | (2006.01) | |
| A61K 31/729 | (2006.01) | |
| A61K 33/38 | (2006.01) | |
| A61K 45/06 | (2006.01) | |
| A61K 9/00 | (2006.01) | |
| A61K 9/14 | (2006.01) | |
| A61K 31/728 | (2006.01) | |

(52) U.S. Cl.
CPC ............. *A61K 31/738* (2013.01); *A61K 31/192* (2013.01); *A61K 31/196* (2013.01); *A61K 31/717* (2013.01); *A61K 31/729* (2013.01); *A61K 33/38* (2013.01); *A61K 45/06* (2013.01); *A61K 9/0014* (2013.01); *A61K 9/146* (2013.01); *A61K 31/728* (2013.01)

USPC ................................ 424/45; 424/618; 514/57

(58) Field of Classification Search
None
See application file for complete search history.

(56) References Cited

U.S. PATENT DOCUMENTS

| | | | |
|---|---|---|---|
| 2004/0001880 A1* | 1/2004 | Bowler et al. ................. | 424/445 |
| 2005/0196455 A1* | 9/2005 | Chen et al. .................... | 424/489 |
| 2010/0317617 A1* | 12/2010 | Mousa et al. .................... | 514/56 |
| 2010/0317652 A1* | 12/2010 | Bryans et al. ................. | 514/218 |
| 2011/0008444 A1* | 1/2011 | Bergman et al. .............. | 424/488 |

FOREIGN PATENT DOCUMENTS

WO    WO 2005/044236 A1    5/2005

OTHER PUBLICATIONS

Carter et al., "Silver treatments and silver-impregnated dressings for the healing of leg wounds and ulcers; A systematic review and meta-analysis," J. Am. Acad. Dermatol, 2010, vol. 63, No. 4, pp. 668-679.
Choi et al., "Formulation and in vivo evaluation of omeprazole buccal adhesive tablet," Journal of Controlled Release, 2000, vol. 68, pp. 405-412.
Collison, D., "Pressure Ulcers," Merck Manual, Oct. 2008, pp. 1-9.
Saxen et al., "Sustained relief of oral aphthous ulcer pain from topical diclofenac in hyaluronan," Oral Surg, Oral Med, Oral Pathol, Oral Radial Endod, 1997; vol. 84, No. 4, pp. 356-361.
Wolf, S., "Burns," Merck Manual, Mar. 2009, pp. 1-7.

* cited by examiner

*Primary Examiner* — David J Blanchard
*Assistant Examiner* — Daniel F Coughlin
(74) *Attorney, Agent, or Firm* — Birch, Stewart, Kolasch & Birch, LLP

(57) ABSTRACT

The invention discloses pharmaceutical compositions in the form of a dusting powder or dry spray, possessing a high absorbent capacity, painkilling activity and wound-healing action, which compositions consist of croscarmellose sodium, a non-steroidal anti-inflammatory drug (NSAID) and hyaluronic acid, and optionally also contain other pharmacologically active substances and/or excipients. The compositions disclosed herein are suitable for use in the treatment of skin lesions wherein the presence of exudate limits wound healing and causes pain; they are therefore particularly suitable for chronic ulcerous skin lesions of various origins and burns.

19 Claims, 2 Drawing Sheets

ABSORBENT DRESSINGS WITH PAINKILLING ACTIVITY

FIELD OF INVENTION

The present invention concerns absorbent pharmaceutical compositions with painkilling activity.

Skin ulcers are difficult wounds, without a spontaneous tendency to heal, which are caused by over 100 disorders; the most common include diabetes, vascular diseases and all disorders that leave the patient bedridden. The most common forms are venous ulcers, which account for 75% of leg ulcers; ulcers associated with diabetic foot, which leads to amputation in 15% of cases; and bedsores, which mainly affect the elderly, and are caused by immobility and malnutrition. In chronic lesions, exudate is always present: it results from increased vascular permeability caused by the action of the vasoactive amines released in the inflammatory reaction during the tissue repair process, and reflects the extent to which the endothelial barrier is altered. The purpose of the exudate is to limit the disease process, prevent the spread of microorganisms, and inhibit the action of harmful antigens by means of an autoimmune mechanism. Increased permeability of the microcirculation, and therefore the quantity of exudate produced, is proportional to the severity of the inflammatory process: in the case of chronic wounds, the prolonged inflammatory state leads to neurogenic inflammation, which triggers pain. The same picture is presented in an even more accentuated form in the case of burns, where the metabolic damage to the microcirculation is significant. In these situations, therefore, pain control primarily requires management of the exudate. Numerous preparations are available on the market for this purpose, ranging from simple collagen-based powder absorbents (Condress®) to more complex products, such as ointments containing microparticles of absorbent polymers (Cadesorb®), or spongy pads (Aquacel®). The effect in all cases is merely to absorb the exudate, but this is not always sufficient to eliminate the pain of the lesion. A polyurethane foam pad containing a non-steroidal anti-inflammatory drug in the form of sodium salt (Biatain Ibu®) is available on the market as an alternative to oral painkillers; after application the pad releases the drug which, being in the form of a salt, dissolves; it is very rapidly released, but equally rapidly washed away from the wound bed; this means that after the initial intense painkilling effect, its activity declines. This dressing, being an opaque pad, also prevents the wound bed from being inspected, and has to be mechanically removed in order to be replaced, which can cause further lesions when it is removed. There is a strongly felt need for dressings for weeping skin lesions which are easy to apply, have a substantial absorbent and preferably also wound-healing action, and have a prolonged painkilling effect. The Applicant has met this need by devising the pharmaceutical composition claimed in the present invention; it is a powder, designed to be administered as such or in the form of a dry spray, which performs a very marked absorbent action due to the presence of croscarmellose sodium, and has a significant painkilling effect performed synergically by an NSAID in acid form and hyaluronic acid, to which a major wound-healing effect is attributed. Croscarmellose sodium (hereinafter called "croscarmellose") is the crosslinked internal derivative of carboxymethylcellulose sodium salt, and this derivatisation gives it its special characteristics as a superdisintegrant agent. Crosslinking reduces its solubility while maintaining unchanged its absorbent properties, which is why croscarmellose is very widely used in pharmaceutical forms such as tablets and capsules. After being swallowing it absorbs water, swells, causes the pharmaceutical form to disintegrate perfectly, and allows the active ingredient to come into contact with the biological fluids. In the present invention, the Applicant has surprisingly discovered that croscarmellose can be used directly on a wound bed to absorb the exudate which, as stated, represents the greatest problem in wound management and the main cause of the pain felt by the patient. To make its painkilling activity even more effective, the Applicant has combined croscarmellose with an acid NSAID, which therefore has free carboxyl groups, such as diclofenac. NSAIDs like diclofenac have a known anti-inflammatory and analgesic effect, and are widely used not only in many osteoarticular disorders but also as analgesics, which are also active at local level. Numerous pharmaceutical compositions and equally numerous pharmaceutical forms for the administration of NSAIDs are known to the prior art, ranging from the classic tablets for oral use to injectable ampoules and forms for topical application such as creams, hydrogels, foams and medicated patches. It should be noted that the topical forms are designed for application to healthy skin. The common feature of this pharmaceutical variety is the presence of an anti-inflammatory drug, always in salified form, precisely because it is most bioavailable after contact with biological fluids; by way of example only, one of the most widely used NSAIDs, diclofenac, is highly soluble in water (25 mg/ml) when salified with sodium and poorly soluble in saline solution (0.03 mg/ml) in its acid form. In the case of oral administration, salification has the further purpose of reducing the irritant effect on the gastric mucosa.

However, the Applicant has unexpectedly discovered, and subsequently demonstrated, that the use of an NSAID (diclofenac or similar) in its acid form, which is therefore poorly soluble in water, allows dressings to be made for topical use which have an effective, prolonged painkilling action, and eliminate the side effects caused by the continuous systemic administration required in the case of chronic skin lesions. The compositions claimed herein also contain a percentage of hyaluronic acid. The multiple biological effects of HA, mainly associated with its chemical nature, are well known: it is a heteropolysaccharide, and therefore a polymer, which can have a wide range of molecular weights (MW) that usually correspond to differentiated biological effects. The term MW means the weight-average molecular weight, calculated by the "intrinsic viscosity" method (Terbojevich et al., *Carbohydr Res*, 1986, 363-377), and it is to this that we refer in the present invention whenever we speak of average MW. The hyaluronic acid used here enhances the absorbent effect of croscarmellose, performs an important wound-healing action, which is particularly desirable in compositions to be applied to open lesions, and acts synergically with diclofenac (or the other NSAIDs used) in pain management. The compositions claimed in the present invention therefore go well beyond the state of the art, providing a dusting powder or dry spray with a prolonged analgesic effect for the treatment of acute and/or chronic painful, exuding skin lesions.

DETAILED DESCRIPTION OF THE INVENTION

The present patent application describes and claims pharmaceutical compositions in the form of a dusting powder or dry spray, which possess:
1. high absorbent capacity
2. a painkilling activity significantly higher than that of the standards on the market (48 vs. 24 hours)
3. wound-healing action
and consist of:
A. croscarmellose sodium
B. a non-steroidal anti-inflammatory drug (NSAID) in acid form, namely one which has free carboxyl groups
C. hyaluronic acid.

Said compositions can also contain pharmacologically active substances and/or excipients of various kinds considered necessary for formulation purposes by the skilled formulator.

The compositions disclosed herein are suitable for use in the treatment of skin lesions wherein the presence of exudate limits wound healing and causes pain; they are therefore particularly suitable for skin lesions such as wounds, acute or chronic ulcers of various etiologies (diabetes, vascular disease, etc.), bedsores, scalds and burns. As previously stated, the pharmaceutical forms preferred by the Applicant for the compositions described above are dusting powder and dry spray, which:
- are very simple to apply;
- make it unnecessary to touch the wound with the hands, thus reducing the risk of bacterial contamination;
- form a layer of transparent gel on the lesion which allows the wound bed to be seen;
- require fewer applications, presenting a definitely long-lasting effect and therefore improve patient compliance;
- are easily formulated, with obvious advantages in terms of industrial manufacture.

Figure 1:
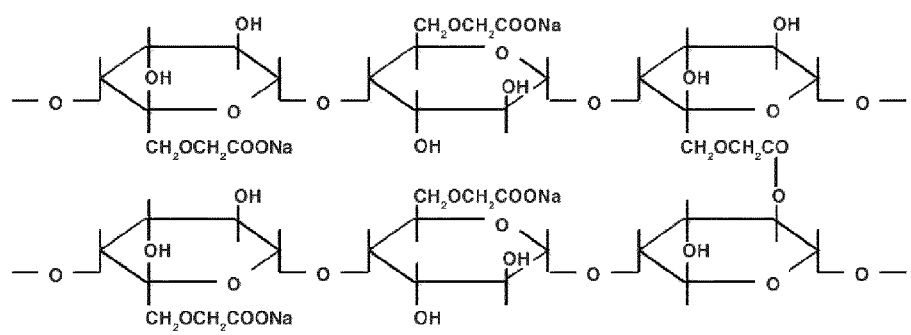
FIG. 1 shows the structure of hyaluronic acid Croscarmellose (CMCC).

As already stated, the pharmaceutical compositions of the invention consist of croscarmellose sodium (hereinafter called "croscarmellose"), an acid non-steroidal anti-inflammatory drug (NSAID) and hyaluronic acid. Croscarmellose (CMCC—FIG. 1), which is widely used in the pharmaceutical industry for its properties as superdisintegrant, is a crosslinked derivative of carboxymethylcellulose; it is insoluble in water and can absorb enormous quantities of fluids. When included in pharmaceutical compositions for oral use, it allows perfect disintegration of the formulation (capsule or tablet) and consequently ensures that the bioavailability of the drug it contains increases due to greater contact with biological fluids. In the present invention, croscarmellose is used directly on an open wound for the opposite purpose: namely to sequester the exudate that always accompanies the lesions, so that the medicament contained in the formulation comes into contact with minimal amounts of liquid to prevent it from being rapidly washed out of the wound. For this reason in the present compositions, croscarmellose accounts for at least 90% by weight (w/w) of the entire composition. Under these circumstances, unlike the situation previously described, the NSAID contained in the formulation is used in its acid form, and is therefore poorly soluble in water; the resulting effect is a calibrated release over time, with an analgesic activity that, evaluated in vitro, lasts for up to 48 hours after administration; the release profile, which will be illustrated below, demonstrates that the quantity of medicament released at local level is sufficient to induce the analgesic effect but, being minimal, prevents systemic absorption, thus avoiding hypothetical side effects. All this also eliminates the need for frequent administration of the medicament. Together with these effects, the presence of hyaluronic acid (HA) in the formulation should be considered. HA is a linear-chain heteropolysaccharide consisting of alternating residues of D-glucuronic acid and N-acetyl-D-glucosamine, with a weight-average molecular weight that can vary between 400 and $3 \times 10^6$ Da, depending on the source of extraction and the preparation method used. Hyaluronic acid can be obtained, for example, by extraction from rooster combs (EP 138572 B1), by fermentation (from *Streptococcus*), or by biosynthesis (from *Bacillus*). As stated, HA is known to perform multiple functions in the body, ranging from mechanical support for the cells of many tissues such as skin, tendons, muscles and cartilage to tissue hydration and joint lubrication. It is also known that HA, through its CD44 membrane receptor, is able to modulate many different cell physiology and biology processes, such as cell proliferation, migration and differentiation and angiogenesis. As already stated, the various effects of HA are attributed to different average MWs. Its role in the wound-healing process is mainly due to the fact that it induces fibroblast migration; it also moderates the inflammatory phase through the activity of free radical scavengers and activation of negative feedback mediated by interaction with specific receptors (Trabucchi et al., *Int J Tissue React*, 2002, 24, 65-71). It also has a wound remodelling effect because it regulates fibrosis by modulating collagen secretion. The indirect effect of hyaluronic acid on pain, which has been demonstrated for years in medical practice relating to the use of intra-articular HA in osteoarthritis, should also be borne in mind; in these cases, suppression of pain is probably due to the viscoelasticity of the products injected, which protects and attenuates the mechanical and chemical stresses transmitted to the nociceptive nerve endings of the inflamed intra-articular area (Gomis et al., *Arthritis Rheumatism*, 2004, 50, 314-326). For intra-articular treatments, hyaluronic acid with a MW ranging between 730,000 and millions of daltons is used.

The pharmaceutical compositions of the present invention therefore not only have the effects attributable to the individual ingredients, but above all have an effective, lasting effect on pain due to the synergy between a classic analgesic, used innovatively in acid form, and hyaluronic acid.

Of the various NSAIDs normally used for pain control, those which possess one or more free acid groups, such as diclofenac, ibuprofen, naproxen and aceclofenac, are suitable for the present pharmaceutical compositions; within that group, the preferred molecule is diclofenac.

In view of the simplicity of preparation of the formulations of the invention, and their ease of application, it would also be possible to combine the formulations of the invention with other pharmacologically active ingredients, especially substances that possess antiseptic, antimicrobial or antifungal properties; in fact, chronic sores and/or ulcers easily become infected or at high risk of infection. In such situations, a pharmaceutical composition which acts on both pain and microbial contamination would be very useful. Silver, whose antimicrobial and antifungal properties are well-known, may be particularly suitable for this purpose. Silver exists on the market in the form of salts (now obsolete) and in the form of colloidal metal (combined with casein) and micronised metal. The most widely used is the latter, which requires no further micronisation, is easily mixed with other powders, and does not stain skin or tissue after application.

For use as an antibacterial agent, silver is generally used at concentrations ranging from 1 to 5% by weight of the total weight of the composition; for the compositions described, the Applicant uses a concentration of micronised metallic silver ranging from 1.5 to 2%, preferably 2% by weight of the total weight of the composition.

Figure 2:
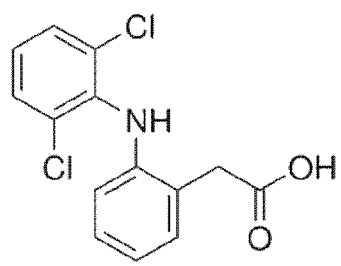
FIG. 2 shows diclofenac in acid form.

As already stated, the pharmaceutical compositions of the invention can take the form of a dusting powder or dry spray; the basic ingredient is croscarmellose (CMCC), pharmaceutical grade, which is widely available on the market in the form of microfibres (e.g. AcDiSol—FMC Biopolymers; Solutab—Blanver). As regards NSAIDs, the one preferred is diclofenac in acid form (FIG. 2), at a concentration ranging from 0.4 to 3% by weight of the total weight of the composition, preferably from 0.6 to 2.4%, and most preferably from 0.8 to 1.2%.

The hyaluronic acid used in this invention is preferably obtained by biosynthesis or fermentation, and has a weight-average molecular weight of between 130 and 230 kDa, preferably between 145 and 210 kDa, and most preferably between 160 and 200 kDa, the latter being indicated simply as average MW 200 kDa. It can be purchased from numerous companies (Lifecore Biomedical; QP Corp.; Seikagaku; Shiseido; Fidia farmaceutici) which are able to provide HA with the desired MW specifications. Hyaluronic acid is used in the present pharmaceutical compositions at a concentration ranging from 0.1 to 4% by weight of the total weight of the composition, preferably from 0.2 to 2%.

A preferred pharmaceutical composition according to the invention comprises croscarmellose sodium at a concentration ranging from 90 to 99.5% by weight of the total weight of the composition, hyaluronic acid having a weight-average molecular weight between 160 and 200 kDa at a concentration ranging from 0.2 to 2% by weight of the total weight of the composition, diclofenac as non-steroidal anti-inflammatory drug in acid form at a concentration ranging from 0.8 to 1.2% by weight of the total weight of the composition. Said preferred composition can also comprise silver at a concentration equal to 2% by weight of the total weight of the composition, said silver being present in form of colloidal metal or micronized metal, preferably in form of micronized metal.

A further object of the present invention are pharmaceutical compositions according as described above for topical use in the treatment of exuding skin lesions.

Said compositions can be formulated as dusting powder or as dry spray. To be formulated as dry spray, the obtained powder is introduced into pressurised canisters (1.3 bars) with n-butane.

The pharmaceutical compositions according to the present invention are preferably in form of a dusting powder.

Some pharmaceutical compositions in the form of dusting powder and dry spray will now be described for the purpose of illustration. Dry spray compositions will include a propellant, in particular n-butane. The release kinetics of the active ingredient of the compositions of the invention is reported hereinbelow.

EXAMPLE 1 preparation of a pharmaceutical composition in powder form containing 0.8% diclofenac acid (DCFH) and 0.2% HA sodium salt (HANa).
Composition:
DCFH 0.24 g
HANa 0.06 g weight-average MW 200 kDa
CMCC q.s. for 30 g
Preparation:
When the ingredients have been weighed, the DCFH, HANa and a first aliquot of CMCC amounting to 15% by weight of the total quantity are poured into a glass beaker equipped with an anchor-shaped magnetic stirrer, and mixed for at least 30 minutes. Three aliquots of CMCC, amounting to 15% by weight of the total quantity, are then added successively, mixing between one addition and the next for at least 1 hour.

Finally, the remaining quantity of CMCC is added, and mixed for at least three hours. The mixture is then stove-dried under vacuum at the temperature of 30° C. for at least 8 hours.

EXAMPLE 2 preparation of a pharmaceutical composition in powder form containing 0.8% diclofenac acid (DCFH) and 1.3% HA sodium salt (HANa).
Composition:
DCFH 0.24 g
HANa 0.39 g weight-average MW 200 kDa
CMCC q.s. for 30 g
Preparation:
When the ingredients have been weighed, the DCFH, pre-micronised HANa and a first aliquot of CMCC amounting to 15% by weight of the total quantity are poured into a glass beaker equipped with an anchor-shaped magnetic stirrer, and mixed for at least 30 minutes. Three aliquots of CMCC, amounting to 15% by weight of the total quantity, are then added successively, mixing between one addition and the next for at least 1 hour.

Finally, the remaining quantity of CMCC is added, and mixed for at least three hours. The mixture is then stove-dried under vacuum at the temperature of 30° C. for at least 8 hours.

EXAMPLE 3 preparation of a pharmaceutical composition in powder form containing 1.2% diclofenac acid (DCFH) and 0.2% HA sodium salt (HANa).
Composition:
DCFH 0.36 g
HANa 0.06 g weight-average MW 200 kDa
CMCC q.s. for 30 g
Preparation:
When the ingredients have been weighed, the DCFH, pre-micronised HANa and a first aliquot of CMCC amounting to 15% by weight of the total quantity are poured into a glass beaker equipped with an anchor-shaped magnetic stirrer, and mixed for at least 30 minutes. Three aliquots of CMCC, amounting to 15% by weight of the total quantity, are then added successively, mixing between one addition and the next for at least 1 hour.

Finally, the remaining quantity of CMCC is added, and mixed for at least three hours. The mixture is then stove-dried under vacuum at the temperature of 30° C. for at least 8 hours.

EXAMPLE 4 preparation of a pharmaceutical composition in powder form containing 0.8% diclofenac acid (DCFH), 0.2% HA sodium salt (HANa) and 2% micronised metallic silver.
Composition:
DCFH 0.24 g
HANa 0.06 g weight-average MW 200 kDa
Micronised metallic silver 0.6 g
CMCC q.s. for 30 g
Preparation:
When the ingredients have been weighed, the DCFH, pre-micronised HANa and a first aliquot of CMCC amounting to 15% by weight of the total quantity are poured into a glass beaker equipped with an anchor-shaped magnetic stirrer, and mixed for at least 30 minutes. The entire quantity of silver is added, followed by three aliquots of CMCC amounting to 15% by weight of the total quantity, mixing between one addition and the next for at least 1 hour.

Finally, the remaining quantity of CMCC is added, and mixed for at least three hours. The mixture is then stove-dried under vacuum at the temperature of 30° C. for at least 8 hours.

EXAMPLE 5 preparation of a pharmaceutical composition in powder form containing 0.8% diclofenac acid (DCFH), 1.3% HA sodium salt (HANa) and 2% micronised metallic silver.
Composition:
DCFH 0.24 g
HANa 0.39 g weight-average MW 200 kDa
Micronised metallic silver 0.6 g
CMCC q.s. for 30 g
Preparation:
When the ingredients have been weighed, the DCFH, pre-micronised HANa and a first aliquot of CMCC amounting to 15% by weight of the total quantity are poured into a glass beaker equipped with an anchor-shaped magnetic stirrer, and mixed for at least 30 minutes. The entire quantity of silver is added, followed by three aliquots of CMCC amounting to 15% by weight of the total quantity, mixing between one addition and the next for at least 1 hour.

Finally, the remaining quantity of CMCC is added, and mixed for at least three hours. The mixture is then stove-dried under vacuum at the temperature of 30° C. for at least 8 hours.

Each of the formulations according to examples 1-3 clearly provides a powder; to be formulated as a dry spray, the powder obtained is introduced into pressurised canisters (1.3 bars) with n-butane.

As stated, the present compositions can also include excipients, lubricants, stabilisers or anything else considered necessary by one skilled in the art to improve the characteristics of the final formulations.

Release of Diclofenac from Formulations According to the Present Invention (in vitro)

The evaluation of the release kinetics of Diclofenac from the formulation was conducted with a Franz cell, comparing the release of the diclofenac contained in the formulation described in example 1 with an identically formulated composition containing diclofenac sodium (DCFNa) instead of diclofenac acid, at the same percentage.

The Franz cell is an instrument known to the skilled person; briefly, and very simply, it consists of two chambers, the lower one being called the receptor, while the upper one is called the donor. The two cells are separated by a porous membrane and connected to one another; the medium in which the diffusion of the active ingredient in question will be evaluated is loaded into the receptor chamber, and the product to be evaluated is loaded into the donor chamber. The medium flows against the separator membrane, and therefore comes into contact with the product loaded into the donor chamber; the active constituent spreads through the membrane to the receptor chamber, from which aliquots are sampled for testing to determine the extent of release of the active ingredient.

In this specific case, the receptor chamber was loaded with rabbit plasma (10.2 ml); approx. 73 mg of the formulation of Example 1 based on diclofenac acid (DCF/H+), accurately weighed, was placed in the donor chamber, distributed on a cellulose acetate membrane with a porosity (cut-off) of 0.2µ, wetted with rabbit plasma, and an area of 3.46 cm2. When the operating procedures of the Franz cell had been activated, 0.3 ml samples of rabbit serum were taken from the receptor chamber, which was topped up with fresh serum from time to time. The diclofenac is determined by spectrophotometric analysis, calibrating the instrument with rabbit plasma to take account of the effect of the medium on the release of the medicament.

The same procedure was followed to measure the release of diclofenac sodium (DCF/Na) formulated identically to the formulation of Example 1 in qualitative and quantitative terms.

Figure 3:
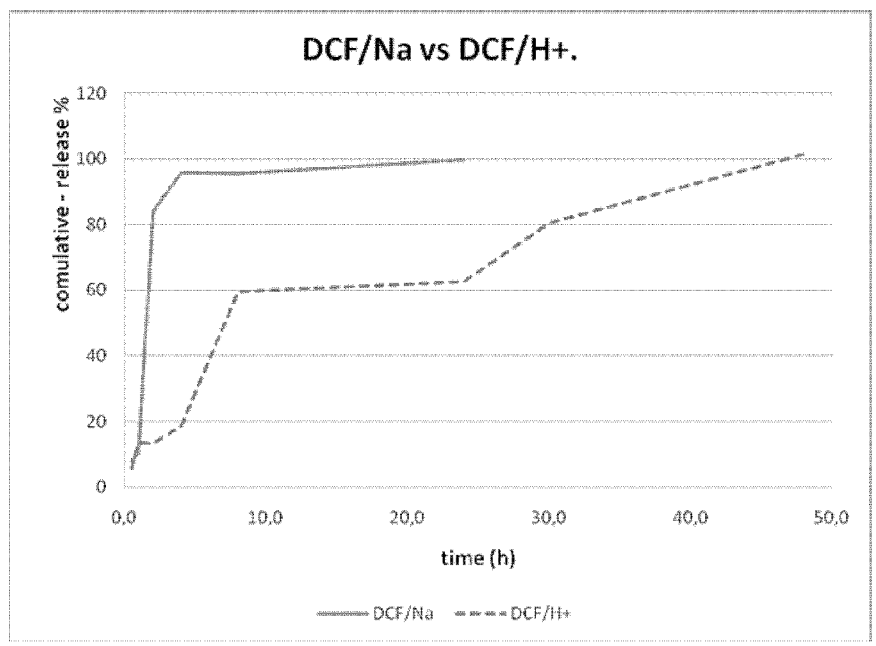
FIG. 3 shows the release of DCFH and DCF-Na from the formulation, evaluated in vitro with Franz cell, in rabbit plasma.

The results of the measurements are set out in FIG. 3 which shows the release of DCFH and DCF-Na from the formulation, evaluated in vitro with a Franz cell, in rabbit plasma. It is clear that diclofenac sodium is released very quickly, due to its very high solubility in water, so that over 90% of the medicament is released in the first 4 hours. There is consequently a massive release of active ingredient, the effect of which is very rapid, but soon disappears; in fact, the drug is exhausted within 24 hours. The presence of such a large amount of medicament is substantially useless, as the pharmacological effect takes place at local level, with minimal concentrations of active ingredient; moreover, such a high concentration may give rise to a degree of systemic absorption, which in turn can generate adverse effects. The release profile is entirely different from that of diclofenac acid; the drug is released gradually, reaching 60% after approx. 8 hours, and the release continues over time, for 48 hours or more. The quantity of medicament present at local level is sufficient to induce the analgesic effect but, being minimal, it prevents the risk of systemic side effects. The formulations described here therefore provide absorbent pharmaceutical compositions which induce gradual, calibrated release of a painkilling NSAID in acid form, in particular diclofenac; the release is long-lasting, being manifested for at least 48 hours after application; twice the effect of the equivalent sodium salt is therefore obtained over time with the same dose of medicament. The pharmaceutical compositions claimed here obviously represent an improvement on the prior art in therapeutic terms (fewer administrations, ease of application, possibility of checking the wound bed), industrial terms (simplicity of formulation and preparation) and social terms (reduction of health spending).

Release of Diclofenac from Formulations According to the Present Invention (in vivo)

The already discussed in vitro data have been confirmed by in vivo tests, following a standard protocol for the evaluation of post-operative pain in the rat, approved by the Committee for Ethical Conduct in the Care and Use of Laboratory Animals. The rat has been selected as it represents the species of choice for this experimental animal model.

Materials and Methods
Species/Strain: 180-200 g weighing 40 SD male rats divided in 4 groups (10 rats per group)
Animals were randomly assigned to experimental groups as follows:
Group 1: Morphine (Positive Control) 5 mg/kg
Group 2: HA+CMCC+Diclofenac in Acidic form (DCFH) 0.8% prepared as described in Ex. 1
Group 3: HA+CMCC+Diclofenac in Acidic form (DCFH) 1.2% prepared as described in Ex. 3
Group 4: HA+CMCC+Diclofenac Sodium (DCF-Na) 0.8% prepared as described in Ex. 1 using DFC-Na instead of DFCH.

Items to be tested are applied once topically on study day 0. The application is performed immediately post surgery inside the incision before suturing the skin lesion (5 mg) and on the top of the sutured lesion (1 mg). Morphine is administered at a dose of 5 mg/kg IP on study day 0 immediately after surgery.

Each dosing group is kept in separate cages to avoid cross-contamination which can occur through consumption of fecal matter.

At the end of the study, surviving animals are euthanized by pentobarbital sodium.

Study Description:
Day −1: body weight measurement and Von Fray (VF) measurement (Baseline)
Day 0: Surgery; application of Items to be tested; application of Morphine (Positive Control); VF measurements at 1 h, 3 h, 6 h, 12, post surgery
Day 1: VF measurements at 24 h
Induction of Post-Operative Pain:

All animals have been anaesthetized by isoflurane. Under anaesthesia, a 1 cm longitudinal incision over the plantar surface of the right hind paw is performed and the plantaris muscle is incised longitudinally. The incision is then closed with two stitches, and the rats are then allowed to recover from general anaesthesia.

Figure 4:
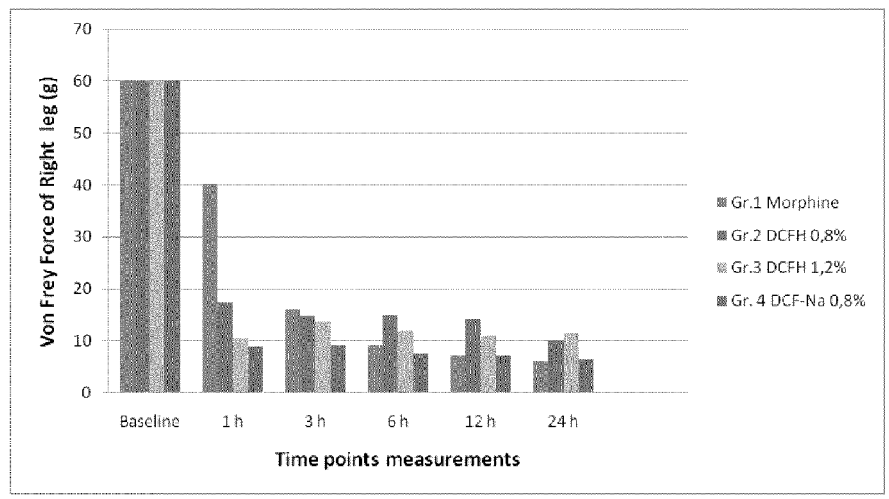
FIG. 4 shows the results of the pain response evaluation.

Pain Response Evaluation:

Allodynic response to tactile stimulation is assessed using the Von Frey apparatus (Touch Test®). The rat is placed in an enclosure and positioned on a metal mesh surface, but allowed to move freely. The rats' cabins are covered with red cellophane to diminish environmental disturbances. The test begins after cessation of exploratory behavior. In brief, Von Frey apparatus includes a set of monofilaments; each filament exerts an increasing force to the plantar surface, starting below the threshold of detection and increasing until the animal removes its paw. The normal animal response, paw withdrawal reflex, is automatically recorded using two metrics: the latency until withdrawal, in seconds, and the force at which the paw was withdrawn, in grams (see FIG. 4).

Then, when the tip of a fiber of given length and diameter is pressed against the skin at right angles, the force of application increases as the researcher continues to advance the probe until the fibre bends. After the fiber bends, the probe continues to advance, causing the fiber to bend more, but without additional force being applied.

Rodents exhibit a paw withdrawal reflex when the paw is unexpectedly touched. The Touch Test® Sensory Evaluator can be used on the plantar surfaces of the rat's foot. The animal indicates sensation by pulling back its paw. The minimal force needed to elevate the withdrawal reflex is considered/designated as the value reference. In order to achieve paw withdrawal, the pressure applied is sometimes higher than 60 g, often requiring the researcher to apply enough pressure with the Von Frey to actually lift the paw of the naive animal. Decreases in the force needed to induce withdrawal are indicative of allodynia, as the force applied is a non-painful stimulus under normal conditions.

The data illustrated in Graph 2 confirm the results previously obtained in vitro using the Franz cell, and precisely:
  the compositions containing DCFH exert painkilling activity, which is already evident starting 1 hour after administration and is constant over time; after 3 hours the painkilling activity is comparable to that of morphine and after 6 hours is even higher;
  the effectiveness of DCFH compositions is always higher than that of DCF sodium compositions, and in particular, at the same concentration, at each time point examined, the DCFH compositions have twice the effect of the corresponding sodium derivative, exactly as outlined by the in vitro tests;
  even after 24 hours the compositions of the invention exert a painkilling activity superior to both that of morphine and that of the analogous DCF sodium composition.

It should be noted that the composition containing DCFH 1.2% by weight has an initial activity lower than that of the same acid 0.8% by weight, while it continues to act up to 24 hours after application; this is justified by the fact that, as the exudate in the wound is reduced by the absorbent action of CMCC, the greater amount of DCFH present is solubilized and released more slowly.

The previously presented data demonstrate therefore that the compositions object of the present invention are endowed with absorbent capacity, with cicatrizing power and especially with high painkilling activity; particularly, the formulations containing DCFH 0.8% by weight have an effect on pain, at the same concentrations, much higher than the commercial standards containing Diclofenac Sodium and represent therefore the preferred compositions.

The invention claimed is:

1. A pharmaceutical composition comprising croscarmellose sodium, hyaluronic acid and a non-steroidal anti-inflammatory drug in acid form for the topical treatment of exuding skin lesions, wherein said croscarmellose represents at least 90% w/w of the composition.

2. The pharmaceutical composition according to claim 1, wherein the non-steroidal anti-inflammatory drug in acid form is at least one member selected from the group consisting of diclofenac, ibuprofen, naproxen and aceclofenac.

3. The pharmaceutical composition as claimed in claim 1, wherein the non-steroidal anti-inflammatory drug in acid form is diclofenac.

4. The pharmaceutical composition as claimed in claim 1, wherein the hyaluronic acid has a weight-average molecular weight (MW) ranging between 130 and 230 kDa.

5. The pharmaceutical composition as claimed in claim 1, wherein the hyaluronic acid has a concentration ranging from 0.1 to 4% by weight of the total weight of the composition.

6. The pharmaceutical composition as claimed in claim 1, wherein the diclofenac has a concentration of from 0.4 to 3% by weight of the total weight of the composition.

7. The pharmaceutical composition as claimed in claim 1, wherein the composition comprises croscarmellose sodium at a concentration ranging from 90 to 99.5% by weight of the total weight of the composition, hyaluronic acid having a weight-average molecular weight of between 160 and 200 kDa at a concentration ranging from 0.2 to 2% by weight of the total weight of the composition, diclofenac as non-steroidal anti-inflammatory drug in acid form at a concentration ranging from 0.8 to 1.2% by weight of the total weight of the composition.

8. The pharmaceutical composition as claimed in claim 1, further comprising a pharmacologically active substance with antiseptic, antimicrobial or antifungal action.

9. The pharmaceutical composition as claimed in claim 8, wherein the antiseptic, antimicrobial or antifungal substance is micronised metallic or colloidal metallic silver at the concentration of from 1 to 5%, by weight of the total weight of the composition.

10. The pharmaceutical composition as claimed in claim 8, wherein the composition comprises croscarmellose sodium at a concentration ranging from 90 to 99.5% by weight of the total weight of the composition, hyaluronic acid having a weight-average molecular weight of between 160 and 200 kDa at a concentration ranging from 0.2 to 2% by weight of the total weight of the composition, diclofenac as non-steroidal anti-inflammatory drug in acid form at a concentration ranging from 0.8 to 1.2% by weight of the total weight of the composition and silver at a concentration equal to 2% by weight of the total weight of the composition, said silver being present in form of micronized metal.

11. The pharmaceutical composition as claimed in claim 1, in the form of dusting powder or a dry spray containing n-butane as propellant.

12. The pharmaceutical composition as claimed in claim 1, in the form of dusting powder.

13. The pharmaceutical compostion according to claim 1 for topical use in the treatment of exuding skin lesions.

14. The pharmaceutical composition as claimed in claim 1, wherein the hyaluronic acid has a weight-average molecular weight (MW) ranging between 145 and 210 kDa.

15. The pharmaceutical composition as claimed in claim 1, wherein the hyaluronic acid has a weight-average molecular weight (MW) ranging between 160 and 200 kDa.

16. The pharmaceutical composition as claimed in claim 1, wherein the hyaluronic acid has a concentration ranging from 0.2 to 2% by weight of the total weight of the composition.

17. The pharmaceutical composition as claimed in claim 1, wherein the diclofenac has a concentration of from 0.6 to 2.4% by weight of the total weight of the composition.

18. The pharmaceutical composition as claimed in claim 1, wherein the diclofenac has a concentration of from 0.8 to 1.2% by weight of the total weight of the composition.

19. The pharmaceutical composition as claimed in claim 8, wherein the antiseptic, antimicrobial or antifungal substance is micronised metallic or colloidal metallic silver at the concentration of 2% by weight of the total weight of the composition.

* * * * *